United States Patent [19]

Aaronson et al.

[11] Patent Number: 5,512,434
[45] Date of Patent: Apr. 30, 1996

[54] EXPRESSION CLONING OF A HUMAN PHOSPHATASE

[75] Inventors: Stuart A. Aaronson, Great Falls, Va.; Donald P. Bottaro, Kensington, Md.; Toshio Ishibashi; Toru Miki, both of Rockville, Md.

[73] Assignee: The United States of America as represented by the Department of Health and Human Services, Washington, D.C.

[21] Appl. No.: 988,273

[22] Filed: Dec. 14, 1992

[51] Int. Cl.$^6$ .............................. C12Q 1/42; C12Q 1/48; C12Q 1/68
[52] U.S. Cl. .................... 435/6; 435/7.1; 435/15; 435/21
[58] Field of Search ................. 435/6, 7.32, 15, 435/21, 29, 7.1

[56] References Cited

U.S. PATENT DOCUMENTS 4,710,469  12/1987  Liang et al. ............................. 435/194
5,294,538  3/1994  Beach ....................................... 435/21

OTHER PUBLICATIONS

Ishibashi, T. et al.; Proc. Natl. Acad. Sci. USA 89:12170–12174 (1992).
Kornbluth, S. et al.; Mol. Cell. Biol. 8:5541–5544 (1988).
Stern, D. F. et al.; Mol. Cell. Biol. 11:987–1001 (1991).
Fischer et al. "Protein Tyrosine Phosphatases: A Diverse Family of Intracellular and Transmembrane Enzymes", Science 253: 401–406 (1991).
Lau et al. "Expression of a Set of Growth–related Immediate Early Genes in BALB/c 3T3 Cells: Coordinate Regulation with c–fos or c–myc", Proc. Nat'l. Acad. Sci. USA 84: 1182–1186 (1987).
Charbonneau et al. "Human Placenta Protein–tyrosine––phosphatase: Amino Acid Sequence and Relationship to a Family of Receptor–like Proteins", Proc. Nat'l. Acad. Sci. USA 86: 5252–5256 (1989).
Krueger et al. "Structural Diversity and Evolution of Human Receptor–like Protein Tyrosine Phosphatases", EMBO J. 9(10): 3241–3251 (1990).
Guan et al. "A Tyr/Ser Protein Phosphatase Encoded By Vaccinia Virus", Nature 350: 359–362 (1991).
Guan et al. "Eukaryotic Proteins Expressed in Escherichia coli: An Improved Thrombin Cleavage and Purification Procedure of Fusion Proteins . . . ", Anal. Biochem. 192: 262–267 (1991).
Bottaro et al. "Characterization of the Receptor for Keratinocyte Growth Factor", J. Biol. Chem. 263: 12767–12770 (1990).
Charles et al. "cDNA Sequence of a Growth Factor–inducible Immediate Early Gene and Characterization of its Encoded Protein", Oncogene 7: 187–190 (1992).
Hakes et al. "New Vectors for High Level Expression of Recombinant Proteins in Bacteria", Anal. Biochem. 202: 293–298 (1992).

Primary Examiner—Robert A. Wax
Assistant Examiner—Eric Grimes
Attorney, Agent, or Firm—Foley & Lardner

[57] ABSTRACT

A method for the identification of related polypeptides, using an function-based selection criterion, is disclosed. A novel human phosphatase, and nucleotide sequences coding therefor, identified by the aforementioned method and designated VHR, is also disclosed.

11 Claims, 6 Drawing Sheets

FIG. 2B

```
                                         M   S   G   S   F   E   L   S   V   Q   D
                                                                 10
GCCGGGGCGTGCAGGGCCCCGCGCCGCCATGTCGGGCTCGTTCGAGCTCTCGGTGCAGGA          60
 L   N   D   L   L   S   D   G   S   G   C   Y   S   L   P   S   Q   P   C   N
         20                              30                              50
TCTCAACGACCTGCTCTCGGACGGCAGCGGCTGCTACAGCCTCCCGAGCCAGCCCTGCAA         120
 E   V   T   P   R   I   Y   V   G   N   A   S   V   A   Q   D   I   P   K   L
                         40                              50                  70
CGAGGTCACCCCGCGGATCTACGTGGGCAACGCGTCTGTGGCTCAGGACATCCCCAAGCT         180
 Q   K   L   G   I   T   H   V   L   N   A   A   E   G   R   S   F   M   H   V
             60                              70                              90
GCAGAAACTAGGCATCACCCATGTGCTGAACGCGGCTGAGGGCAGGTCCTTCATGCACGT         240
 N   T   N   A   N   F   Y   K   D   S   G   I   T   Y   L   G   I   K   A   N
                 80                             100                         110
CAACACCAATGCCAACTTCTACAAGGACTCCGGCATCACATACCTGGGCATCAAGGCCAA         300
 D   T   Q   E   F   N   L   S   A   Y   F   E   R   A   A   D   F   I   D   Q
                    100                             120                      130
CGACACACAGGAGTTCAACCTCAGCGCTTACTTTGAAAGGGCTGCCGACTTCATTGACCA         360
 A   L   A   Q   K   N   G   R   V   L   V   H   C   R   E   G   Y   S   R   S
                        120                             140                  150
GGCTTTGGCTCAAAAGAATGGCCGGGTGCTCGTCCACTGCCGGGAAGGTTATAGCCGGTC         420
 P   T   L   V   I   A   Y   L   M   M   R   Q   K   M   D   V   K   S   A   L
                            140                             160             170
CCCAACGCTAGTTATCGCCTACCTCATGATGCGGCAGAAGATGGACGTCAAGTCTGCCCT         480
 S   I   V   R   Q   N   R   E   I   G   P   N   D   G   F   L   A   Q   L   C
                                160                             180
GAGCATCGTGAGGCAGAACCGTGAGATCGGCCCCAACGATGGCTTCCTGGCCCAGCTCTG         540
 Q   L   N   D   R   L   A   K   E   G   K   L   K   P   *
                                    180
CCAGCTCAATGACAGACTAGCCAAGGAGGGAAGTTGAAACCCTAGGGCACCCCACCGC          600
CTCTGCTCGAGAGTCCGTGGGGAGGCCGTGGGAAAGGTGTCCGAGCTGCCATGTTTAG          660
GAAACACACTGTACCCTGCTCCCAGCATCACAAGGCACTTGTCTACAAGTGTCCCAAC          720
ACAGTCCTGGGCCACTTCCCCACCCTGTCCGTTTCTGTAACTTATGTGTCTTTCCCAAC        780
GTCCTTGCTCCCCAGTTGTCCGTTTCTGTAACTTATGTGTCTTTCCCTGAGATGGGG         840
GCTCAGAGGGGAAGGCCTGT                                              861
```

FIG. 3

```
VHR    59  VLNAAEGRSFMHVNTNANFYKDSGITYLGIKANDTQEFNLSAYFERAADFIDQALAQKNG
3CH134 194 MLDALGITALINVSANCPNHFEGHYQYKSIPVEDNHKADISSWFNEAIDFID-SIKDAGG
VH1    46  PSSEVKFKYVLNLTMDKYTLPNSNINIIHIPLVDDTTTDISKYFDDVTAFLSKC-DQRNE
               *        *         *           *         *         *

VHR    119 RVLVH C REGYSRSPTLVIAYLMRQKMDVKSALSIVRQNREIG-PNDGFLAQLCQLND
3CH134 253 RVFVH C QAGISRSATICLAYLMRTNRVKLDEAFEFVKQRRSIISPNFSFMGQLLQFES
VH1    105 PVLVH C AAGVNRSGAMILAYLMSKNKESLPMLYFLYVYHSMRD-LRGAFVENPSFKRQ
       *   *   *        **  **      *       *                *
```

FIG. 4

EXPRESSION CLONING OF A HUMAN PHOSPHATASE

BACKGROUND

The identification of related polypeptides has been accomplished mainly through methods of nucleic acid hybridization. Although a powerful tool that has resulted in the identification and characterization of many protein families, nucleic acid hybridization is limited by the requirement that structural similarity exist between the probe nucleic acid and the target nucleic acid. While conditions may be adjusted to vary the amount of similarity needed before hybridization occurs, a certain threshold sequence homology is needed for meaningful identification. When the degree of similarity falls below this threshold, identified polypeptides are less likely to truly be related in structure, evolution, and function. Moreover, even proteins that may be significantly related in structure may be overlooked if the nucleic acid probe happens to be from a region of low homology.

By way of contrast, using functional similarity as the key to relate families of polypeptides obviates concerns about both false positive and false negative identification. While the level of function may vary, a polypeptide either possesses the function of interest or it does not. And the presence of a given function demonstrates that a protein is significantly related to other proteins expressing a similar function, regardless of structure. A strategy for the identification of related proteins that uses the presence of a certain function as the selection criteria would constitute a significant advance over the prior art methods of hybridization identification.

Phosphorylation of tyrosine residues in proteins plays a critical role in fundamental cell functions. Hanks et al., *Science* 241:42–52 (1988); Ullrich and Schlessinger, *Cell* 61:203–212 (1990); Aaronson, *Science* 254:1146phosphorylation is often transient, being regulated within the cell by protein tyrosine kinases ("PTK's") and protein tyrosine phosphatases ("PTP's"). Fischer et al., *Science* 253:401–406 (1991); Hunter, *Cell* 58:1013–1016 (1989). Recently, attention has been directed to the PTP family which, like PTK's, has been implicated in cell signalling, cell growth and proliferation, and oncogenic transformation. Moreover, recent discoveries have shown that some PTP's can be involved in cell-cycle regulation and embryogenesis. Kumagai and Dunphy, *Cell* 64:903–914 (1991); Gould and Nurse, *Nature* 342:39–45 (1989); Dunphy and Newport, *Cell* 58:181–191 (1989); Yang et al., *Cell* 67:661–673 (1991); Tian et al., *Cell* 67:675–685 (1991). Because of these attributes, abnormalities in PTP's are considered as potential causes of cancer and other diseases.

Members of the PTP family have, heretofore, been identified by laborious protein purification protocols and genetic complementation in yeast. Fischer et al. (1991); Lau and Nathans, *Proc. Nat'l Acad. Sci. U.S.A.* 84:1182–1186 (1987). However, the great majority have been identified on the basis of similarities in nucleic acid sequence. To date, these proteins have been observed to share a sequence similarity in their catalytic domains. Charbonneau et al., *Proc. Nat'l Acad. Sci. U.S.A.* 86:5252–5256 (1989); Krueger et al., *EMBO J.* 9:3241–3251 (1990). Due to limitations that apply to identification of PTP's by structural homology, however, it is possible that other PTP's, having significantly less structural homology, have been overlooked.

SUMMARY OF THE INVENTION

It is, therefore, an object of the present invention to provide a method for the identification of DNA sequences encoding substrate-modifying proteins, where the identification depends upon the functional, and not structural, similarity with known substrate-modifying proteins.

Another object of the present invention is to provide a method for the identification of DNA sequences encoding negative modulators of phosphorylation, where the identification depends upon functional, and not structural, similarity with known negative modulators of phosphorylation.

Another object of the present invention is to provide a novel DNA molecule encoding a novel human phosphatase, designated VHR.

Another object of the present invention is to provide a novel human phosphatase, designated VHR.

Another object of the present invention is to provide a method for the diagnosis of a VHR-related disease.

Another object of the present invention is to provide a method for the treatment of a VHR-related disease.

In satisfying the foregoing objects, there has been provided, in accordance with one aspect of the present invention, a method for identifying a DNA encoding a first protein comprising
  (a) selecting a substrate which is modified by said first protein,
  (b) transfecting or infecting a bacterial host with a phagemid comprising
    (i) an origin of replication;
    (ii) a DNA test molecule; and
    (iii) a regulatory region which results in the expression of a protein encoded by said test molecule,
  (c) culturing the transfected or infected bacterial host in the presence of the unmodified from of said substrate such that phagemid-induced plaques are formed and said first protein and said substrate are brought in contact with each other;
  (d) screening the resulting phagemid plaques to identify plaques that contain the modified form of said substrate; and
  (e) isolating phagemid DNA from plaques which contain the modified form of said substrate, whereby said isolated phagemid DNA encodes said first protein.

In addition, there has been provided a method wherein said screening comprises treating phage plaques with antibodies that bind the unmodified form of said substrate and do not bind the modified form of said substrate.

In addition, there has been provided a method for identifying a DNA encoding a first protein, comprising
  (a) selecting a substrate which is modified by said first protein,
  (b) transforming a bacterial host with a plasmid comprising
    (i) an origin of replication;
    (ii) a selectable marker;
    (iii) a DNA test molecule; and
    (iv) a regulatory region which results in the expression of a protein encoded by said test molecule,
  (c) culturing the transformed bacterial host, under selective conditions, in the presence of the unmodified form of said substrate such that plasmid-containing colonies are formed;
  (d) treating said colonies to bring said first protein and said substrate in contact with each other;
  (e) screening the said colonies to identify colonies that contain the modified form of said substrate; and
  (f) isolating plasmid DNA from colonies which contain the modified form of said substrate, whereby said isolated-plasmid DNA encodes said first protein.

In addition, there has been provided a method, wherein said screening comprises treating bacterial colonies with antibodies that bind the unmodified form of said substrate and do not bind the modified form of said substrate.

In addition, there has been provided a method wherein said first protein is a negative modulator of phosphorylation and said substrate is a second protein, wherein said second protein is expressed by said bacterial host, phosphorylated when unmodified and unphosphorylated when modified.

In addition, there has been provided an isolated polynucleotide molecule comprising the following nucleotide sequence (SEQ ID NO:6)

GTGCTCGTCCACTGCCGGGAAGGTTAT-
AGCCGCTCCCCAACGCTA.

In addition, there has been provided an isolated polynucleotide molecule comprising the following nucleotide sequence (bases 29-583 of SEQ ID NO:1)

```
ATGTCGGGCTCGTTCGAGCTCTCGGTGCAGGATCTCAACGACCTG
CTCTCGGACGGCAGCGGCTGCTACAGCCTCCCGAGCCAGCCCTGC
AACGAGGTCACCCCGCGGATCTACGTGGGCAACGCGTCTGTGGCT
CAGGACATCCCCAAGCTGCAGAAACTAGGCATCACCCATGTGCTG
AACGCGGCTGAGGGCAGGTCCTTCATGCACGTCAACACCAATGCC
AACTTCTACAAGGACTCCGGCATCACATACCTGGGCATCAAGGCC
AACGACACACAGGAGTTCAACCTCAGCGCTTACTTTGAAAGGGCT
GCCGACTTCATTGACCAGGCTTTGGCTCAAAAGAATGGCCGGGTG
CTCGTCCACTGCCGGGAAGGTTATAGCCGCTCCCCAACGCTAGTT
ATCGCCTACCTCATGATGCGGCAGAAGATGGACGTCAAGTCTGCC
CTGAGCATCGTGAGGCAGAACCGTGAGATCGGCCCCAACGATGGC
TTCCTGGCCCAGCTCTGCCAGCTCAATGACAGACTAGCCAAGGAG
GGGAAGTTGAAACCC.
```

In addition, there has been provided an isolated polynucleotide molecule that hybridizes, under stringent conditions, with the following nucleotide (bases 29-583 of Seq ID NO:2)

```
ATGTCGGGCTCGTTCGAGCTCTCGGTGCAGGATCTCAACGACCTG
CTCTCGGACGGCAGCGGCTGCTACAGCCTCCCGAGCCAGCCCTGC
AACGAGGTCACCCCGCGGATCTACGTGGGCAACGCGTCTGTGGCT
CAGGACATCCCCAAGCTGCAGAAACTAGGCATCACCCATGTGCTG
AACGCGGCTGAGGGCAGGTCCTTCATGCACGTCAACACCAATGCC
AACTTCTACAAGGACTCCGGCATCACATACCTGGGCATCAAGGCC
AACGACACACAGGAGTTCAACCTCAGCGCTTACTTTGAAAGGGCT
GCCGACTTCATTGACCAGGCTTTGGCTCAAAAGAATGGCCGGGTG
CTCGTCCACTGCCGGGAAGGTTATAGCCGCTCCCCAACGCTAGTT
ATCGCCTACCTCATGATGCGGCAGAAGATGGACGTCAAGTCTGCC
CTGAGCATCGTGAGGCAGAACCGTGAGATCGGCCCCAACGATGGC
TTCCTGGCCCAGCTCTGCCAGCTCAATGACAGACTAGCCAAGGAG
GGGAAGTTGAAACCC.
```

In addition, there has been provide an isolated polypeptide comprising the following amino acid sequence (residues 120-134 of Seq ID NO:2):

V LVHCREGYSR SPTL.

QKNGRV LVHCREGYSR SPTLVIAYLM MRQK.

In addition, there has been provided an isolated polypeptide comprising the following amino acid sequence (SEQ ID NO:2):

```
MSGSFELSVQ DLNDLLSDGS GCYSLPSQPC NEVTPRIYVG NASVAQDIPK
LQKLGITHVL NAAEGRSFMH VNTNANFYKD SGITYLGIKA NDTQEFNLSA
YFERAADFID QALAQKNGRV LVHCREGYSR SPTLVIAYLM MRQKMDVKSA
LSIVRQNREI GPNDGFLAQL CQLNDRLAKE GKLKP.
```

In addition, there has been provided an isolated polypeptide comprising the following amino acid sequence (residues 115-144 of Seq ID NO:2):

In addition, there has been provided an isolated polynucleotide molecule encoding the following amino acid sequence (SEQ ID NO:2:

MSGSFELSVQ DLNDLLSDGS GCYSLPSQPC NEVTPRIYVG NASVAQDIPK
LQKLGITHVL NAAEGRSFMH VNTNANFYKD SGITYLGIKA NDTQEFNLSA
YFERAADFID QALAQKNGRV LVHCREGYSR SPTLVIAYLM MRQKMDVKSA
LSIVRQNREI GPNDGFLAQL CQLNDRLAKE GKLKP.

In addition, there has been provided a method for the diagnosis of a VHR-related disease by in situ hybridization of a DNA probe to the cell or tissue sample of an affected subject.

In addition, there has been provided a method for the diagnosis of a VHR-related disease by in vitro hybridization of a DNA probe to the cell or tissue sample of an affected subject.

In addition, there has been provided a method for the treatment of a VHR-related disease by expressing an recombinant RNA comprising the complement of the following nucleotide sequence (bases 29-43 of Seq ID NO:1:

ATGTCGGGCTCGTTC.

in a cell of an affected subject.

Figure 1:
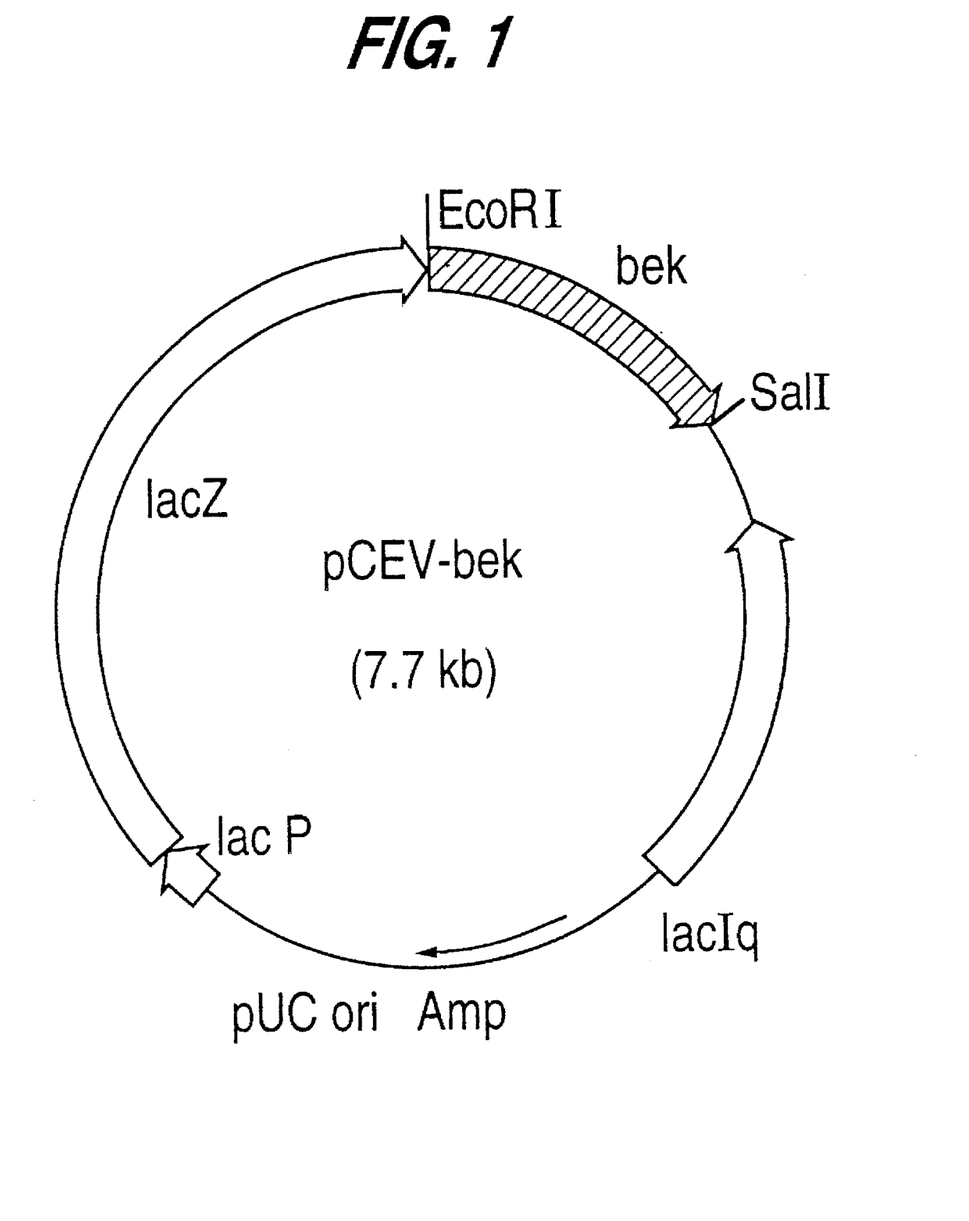

In addition, there has been provide a method for the treatment of a VHR-related disease by expression of recombinant RNA comprising the following amino acid sequence (SEQ ID NO:2:

control of the IPTG-inducible lac promoter. Shaded arrow, cytoplasmic domain of KGF receptor (bek); lacP, lacZ promoter; lacZ, the structural gene for β-galactosidase; lacIq, lac repressor overproducer; Amp, ampicillin resistance.

FIG. 2. VHR nucleotide sequence and predicted primary structure. (A) VHR cDNA is schematically shown with selected restriction sites. The open box represents coding sequences, while noncoding sequences are shown by adjoining lines. Clones 12 and 27, used for sequence analysis, are shown below. (B) Nucleotide and predicted amino acid sequence (SEQ ID NOS 1 and 2) of VHR CDNA. Amino acids are indicated in single-letter code and numbered above the sequence. Stop codon is indicated by an asterisk.

FIG. 3. Sequence comparison of VHR (SEQ ID NO:3) with predicted 3CH134 (SEQ ID NO:4) and VH1 (SEQ ID NO:5) gene products. Amino acid sequence is shown in single-letter code and numbered at left. Boldface type high- MSGSFELSVQ DLNDLLSDGS GCYSLPSQPC NEVTPRIYVG NASVAQD
LQKLGITHVL NAAEGRSFMH VNTNANFYKD SGITYLGIKA NDTQEFNLSA
YFERAADFID QALAQKNGRV LVHCREGYSR SPTLVIAYLM MRQKMDVKSA
LSIVRQNREI GPNDGFLAQL CQLNDRLAKE GKLKP.

in a cell of an affected subject.

Figure 3:
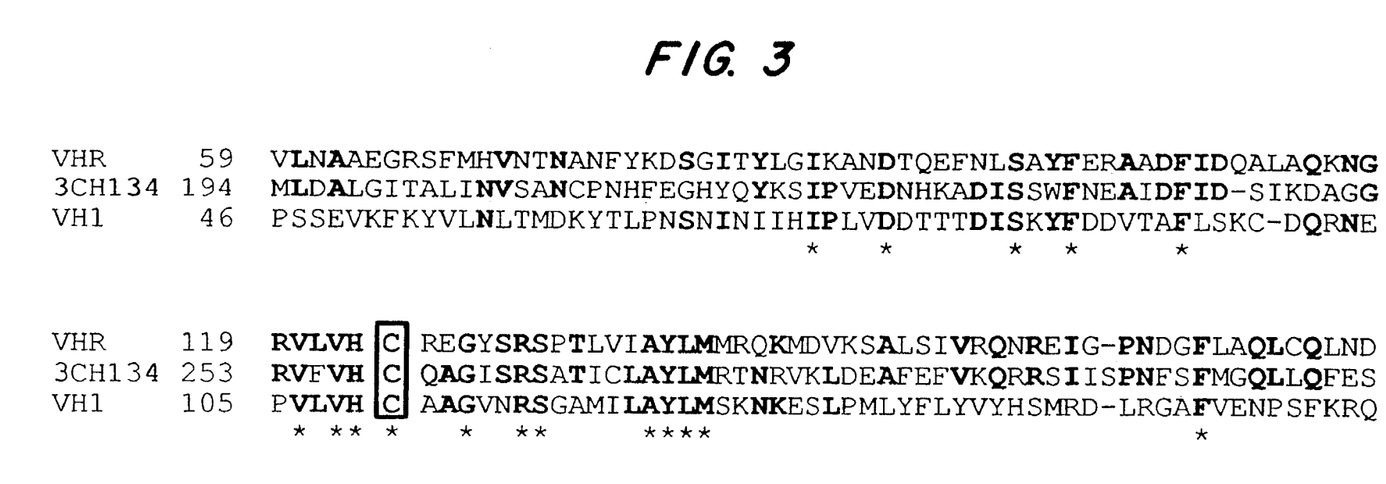

In addition, there has been provided a method for the treatment of a VHR-related disease by administration of an effective amount of a polypeptide comprising the following amino acid sequence (SEQ ID NO:2):

lights residues found in at least two of the sequences, while identities between all three are indicated by asterisks.

FIG. 4. Phosphatase activity of purified VHR. GST-VHR fusion protein and GST were expressed in bacteria and purified in parallel using glutathione-agarose as described in MSGSFELSVQ DLNDLLSDGS GCYSLPSQPC NEVTPRIYVG NASVAQDIPK
LQKLGITHVL NAAEGRSFMH VNTNANFYKD SGITYLGIKA NDTQEFNLSA
YFERAADFID QALAQKNGRV LVHCREGYSR SPTLVIAYLM MRQKMDVKSA
LSIVRQNREI GPNDGFLAQL CQLNDRLAKE GKLKP.

to an affected subject, in a pharmaceutically acceptable carrier.

Figure 4:
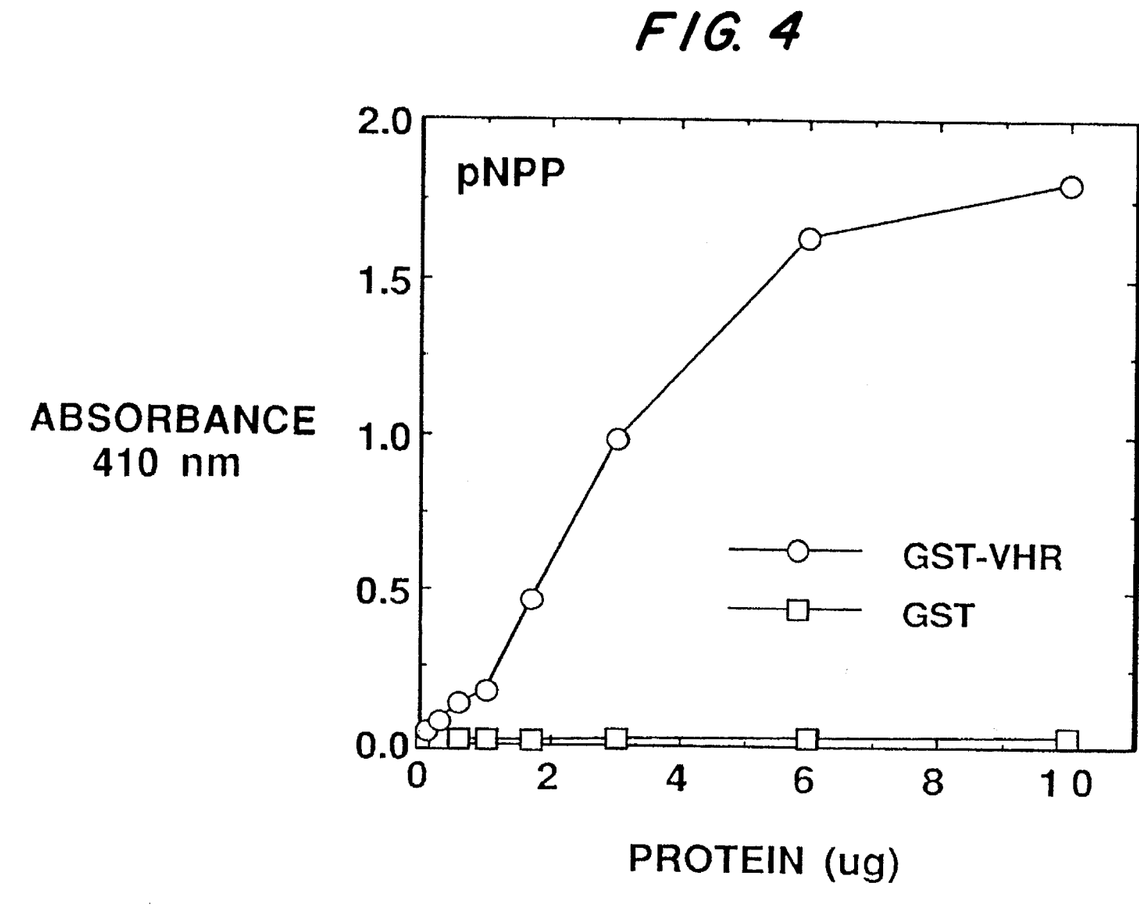

In addition, there has been provided a method for the treatment of a VHR-related disease by administration of an effective amount of an antibody which binds the following amino acid sequence:

the Examples. Dephosphorylation of pNPP, expressed as increased absorbance at 410 nm, was measured as a function of protein concentration. The results shown are representative of three independent experiments.

FIG. 5. Hydrolysis of phosphotyrosine and phosphoserine by VHR. [$^{32}$P]-Phosphocasein was prepared using cAMP- MSGSFELSVQ DLNDLLSDGS GCYSLPSQPC NEVTPRIYVG NASVAQDIPK
LQKLGITHVL NAAEGRSFMH VNTNANFYKD SGITYLGIKA NDTQEFNLSA
YFERAADFID QALAQKNGRV LVHCREGYSR SPTLVIAYLM MRQKMDVKSA
LSIVRQNREI GPNDGFLAQL CQLNDRLAKE GKLKP.

to an affected subject, in a pharmaceutically acceptable carrier.

BRIEF DESCRIPTION OF THE DRAWINGS

FIG. 1. Structure of pCEV-bek. The plasmid pCEV-bek contains a lac repressor and the cytoplasmic domain of the mouse KGF receptor fused in frame to the lacZ gene under dependent protein kinase as described in the Examples. Phosphorylation exclusively on serine was confirmed by phosphoamino acid analysis (data not show). Substrate was incubated with purified VHR (wild-type) or VHR/Ser124 (mutant), and dephosphorylation (expressed as [$^{32}$P]-phosphate release) was measured as a function of enzyme concentration. Results are representative of several experiments. Mutation of Cys to Ser at position 124 of VHR also abolished pNPPase activity (data not shown).

DETAILED DESCRIPTION OF THE INVENTION

The method of "expression cloning," disclosed herein, overcomes the major drawbacks of gene identification based solely on structural homology. Because this approach is based on function rather than sequence similarity, it offers the possibility of identifying PTP's which may be only distantly related, structurally and evolutionarily, to known PTP's. It also lessens the chance that "false" homologs, nucleotide sequences which exhibit limited stretches of high homology to the probe but are otherwise unrelated to the gene from which the probe is derived, will be identified. The use of prokaryotic expression cloning also affords the opportunity to rapidly produce large amounts of quantities of the protein once it has been identified.

The phosphatase identified, designated VHR, bears very little sequence similarity to known PTP's. Therefore, the DNA sequence from which VHR is derived can serve as a probe to discover other members of this family. Because of the role these enzymes play in cell regulation, there is a distinct possibility that aberrations in VHR function play roles in cell transformation and oncogenesis, as well as other disease states. Therefore, the VHR gene and protein should serve as important tools in diagnosis and therapy of VHR-related disease.

A. "Expression cloning"

The identification of genes expressing functional proteins, according to the present invention, is effected with a system with the following characteristics: (i) a set of the DNA sequences to be examined (ii) contained in vectors that express polypeptides encoded by the DNA sequences, (iii) a substrate which can be modified from one form to another, and (iv) a method for differentiating two forms of the substrate. If these four requirements are met, the present invention may be practiced in a variety of embodiments, apparent to those skilled in the art, some of which are described below.

When speaking of "identifying a DNA encoding a protein," the present invention should not be taken as limited to the situation where neither the DNA nor the protein is "known," meaning that they have not previously been sequenced, isolated, or otherwise recognized. While the present invention provides for the identification of "unknown" genes and proteins, it is equally as useful in the determination of functions for "known" genes or proteins for which functions may not have been completely recognized. Thus, the library of sequences to be examined could represent any set of DNA's of interest, but would normally be the cDNA products of reverse transcription. Miki et al., *Gene* 83:137–146 (1989).

The vectors which contain the DNA sequences to be examined must be capable of expressing polypeptides encoded therein. At a minimum, this would require a prokaryotic promoter sequence which initiates transcription of the inserted DNA sequences. A preferred embodiment of the expression vector is one where the expression is inducible to high levels. This is accomplished by the addition of a regulatory region which provides increased transcription of downstream sequences under appropriate stimulation. A more preferred embodiment of the expression vector is a phagemid such as λpCEV-lacZ. This vector has the advantages of tolerating large DNA inserts, inducible high levels of expression, directional insertion of DNA sequences, low background, and easy rescue into sequencing vectors. Should plasmids be used as vectors, growth of plasmid-containing bacteria under selective conditions, usually antibiotic selection, would be necessary.

The expression vectors must be established within the bacterial host in order for expression to commence. This can occur by any standard DNA transfer technique. For phagemids, bacterial cells are transfected or infected with the expression vector or expression vector-containing phage, respectively. With plasmids, transformation, protoplast fusion, or electroporation would be the preferred mechanisms for transfer of the vector into the host. Once established, a culture period sufficient for the expression of the protein encoded by the polynucleotide test molecule is necessary. In the case where phagemids are employed, the lysis of host cells to form a plaque is also accomplished during culture. Likewise, methods employing plasmids require a sufficient period of culture, under selection, for bacterial host colonies to form. All of the above methods are well known in the art. See, for example, Sambrook et al., *MOLECULAR CLONING, A LABORATORY MANUAL,* Second Edition, Vol. 1–3 (Cold Spring Harbor Laboratory, 1989).

The substrate is used as an appropriate indicator of some activity in the plaques or colonies being screened. However, it must be accessible to the polypeptide produced by the expression vector and to the substance used for detection. In the more preferred embodiment, where the expression vector is a phagemid, bacterial hosts are lysed by the phage infection and, therefore, the substrate could be present in the host cell or in media, on or in which the phagemid-containing hosts are incubated. In Example 1, the substrate is a fusion protein designated β-gal-bek, produced by the bacteria, which is an autophosphorylating kinase. Where the expression vectors are plasmids, the substrate would be present within the bacterial host. Alternatively, if plasmid-expressed protein were secreted or the bacterial hosts were artificially lysed, substrate could be supplied in the media.

Once the polypeptide expressed by the vector and the substrate have an opportunity to interact, and any modification of the latter by the former takes place, the detection of the condition of the substrate may take place. The modified condition of the substrate can be simply the absence of the substrate. Alternatively, chemical variation of the substrate, including any eukaryotic posttranslational modification in the case of a protein substrate, can be the indicative state so long as it provides sufficiently sensitive for detection.

Detection can comprise treatment of the plaques or colonies with a chemical that gives, for example, a colorimetric or fluorescent indication of the state of the substrate. As another example, the substrate itself may be an enzyme and the indicative state could be enzymatic activity.

Alternatively, an immunologic determination of the state of the substrate can be made. Where antibodies are available that can distinguish between the modified and unmodified forms of the substrate, colonies or plaques containing a functional polypeptide of interest can be identified by differential binding of antibodies. Immunodetection is the preferred method of detection.

Reference to antibodies is meant to include whole polyclonal and monoclonal antibodies, and parts thereof, either alone or conjugated with other moieties. Antibody parts include Fab and F(ab)$_2$ fragments and single chain antibodies. The antibodies may be made in animals or by recombinant DNA techniques. Other moieties to which antibodies may be conjugated include detectable labels, such as enzymatic labels and fluorescent labels. Radionuclides are other useful labels which can be conjugated to antibodies.

Antibody binding conditions generally are well known in the art and, for the most part, will include neutral pH, moderate salt, temperatures between 2°–3° C. and 37° C., incubation times between several minutes and overnight or longer. It will be readily appreciated by those of ordinary skill in the art that the details of an antibody binding procedure may be adjusted to favor improved signal to noise ratios or sensitivity, rapidity or completeness, and the like. Moreover, conditions may be adjusted to accommodate different procedures for fixation and staining. Finally, it will be appreciated that titers and appropriate dilutions will be different for different antibody preparations.

Once DNA sequences encoding polypeptides with the desired function are identified, the expression vectors described above permit the production of large quantities of the polypeptide. Alternatively, the identified DNA sequences can be recloned into other expression vectors with characteristics that permit higher levels of, or more efficient expression of the polypeptide encoded therein. Depending on the particular physical characteristics of the polypeptide, a variety of different protein purification protocols, all known to those skilled in the art, can be employed to purify the polypeptide. The protocols include, ultrafiltration, high performance liquid chromatography, ion exchange chromatography, affinity chromatography, pseudoaffinity chromatography, immunoaffinity chromatography, gradient centrifugation, and others. Ausubel et al. (eds.), *CURRENT PROTOCOLS IN MOLECULAR BIOLOGY*, Chapter 10, (John Wiley and Sons, 1992).

B. VHR

Using the expression cloning method described above, DNA sequences encoding a polypeptide that reduced phosphorylation of the marker protein β-gal-bek were identified. This protein, therefore, was identified as a negative modulator of phosphorylation. As described in Examples 3 and 4, the function was more specifically defined as phosphatase activity.

Figure 2A:
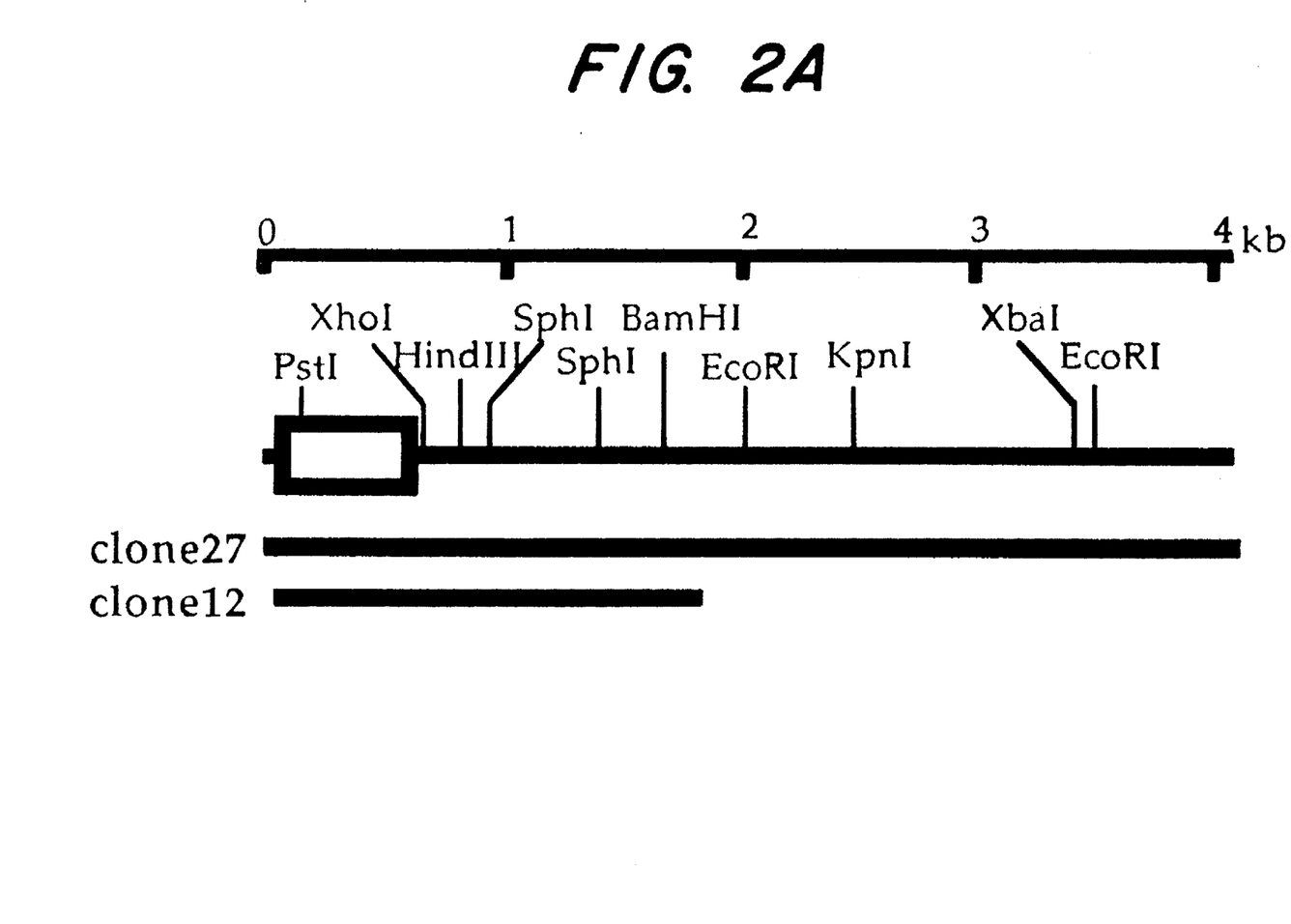
Figure 2B:
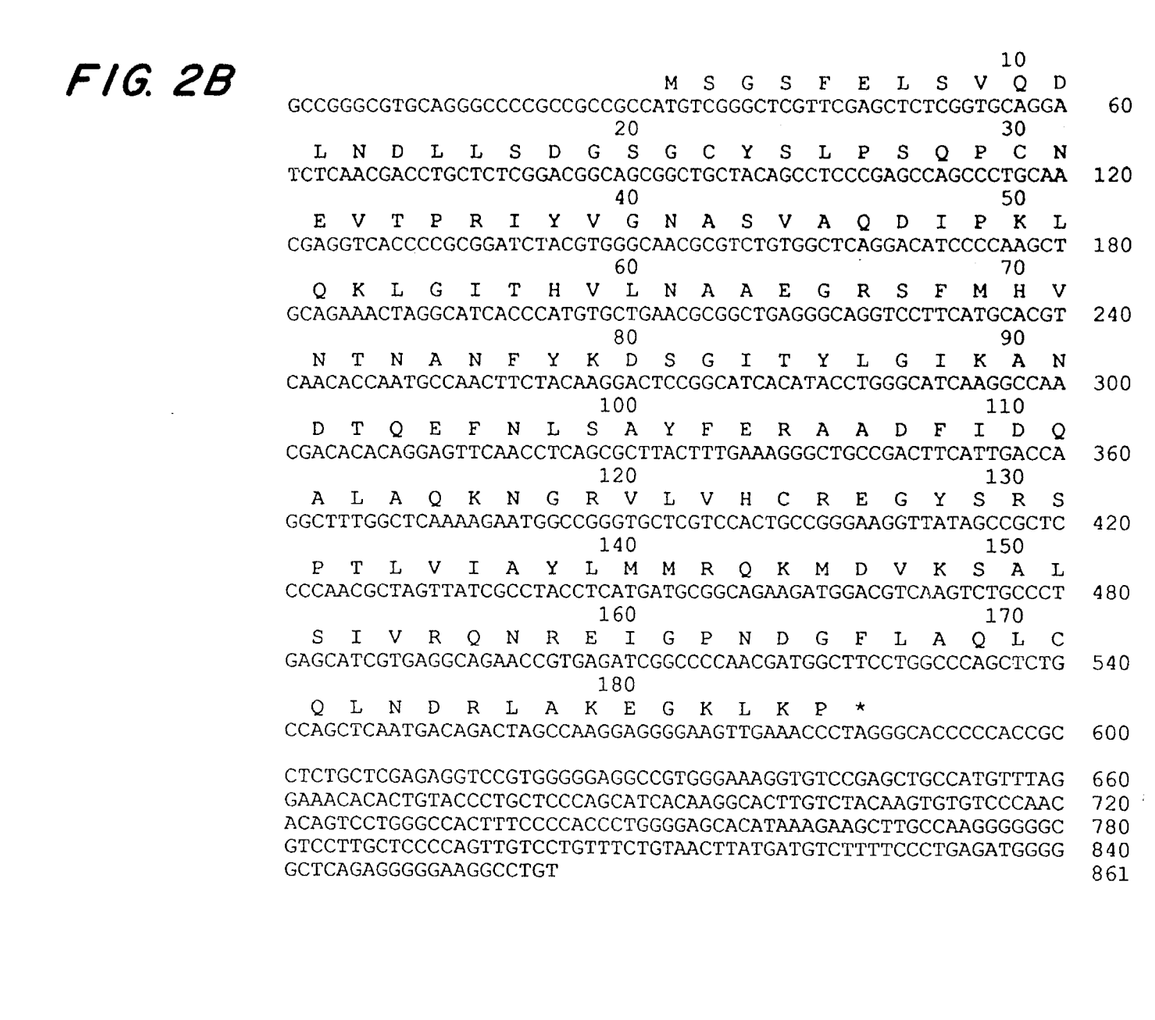

The VHR nucleotide sequence predicts a 185 amino acid protein, most similar biochemically to a phosphatase encoded by the vaccinia virus late gene, H1. Guan et al., Nature 350:359–362 (1991). VHR appears to be lacking a hydrophobic leader sequence characteristic of transmembrane and secreted proteins. FIG. 2 (SEQ ID NOS 1 and 2). Therefore, it is likely that VHR is a cytosolic protein. The nucleotide sequence predicts four cysteine residues, thus creating the potential for two intramolecular disulfide bridges. FIG. 2 (SEQ ID NOS 1 and 2).

VH1 is a 20 kD PTP only distantly related to the eukaryotic PTP's, which efficiently dephosphorylates both phosphotyrosine and phosphoserine containing substrates in vitro. Guan et al. (1991). VHR also exhibits this dual phosphorylation profile, as described in Example 4. Like VH1, mutation of an essential cysteine of VHR completely abolished serine and tyrosine phosphatase activity. Based on these similarities, it is possible that the vaccinia VH1 gene is related to VHR and was acquired by gene transfer between the virus and host, as has been postulated for other vaccinia genes. Biasco, "Evolution of poxviruses and African swine fever virus," in *Molecular Evolution of Viruses*, Cambridge University Press (in press).

Because PTP's are known to affect cell regulation, they can be used as markers for VHR-related disease. Therefore, one use for VHR nucleic acid sequences is as probes for the VHR gene and its transcripts. For instance, alterations in the VHR gene can be detected directly after purification of whole cell DNA by Southern blotting procedures. In addition, changes in VHR RNA levels can be assessed by Northern blot analysis in intact cells or with isolated RNA. Tissue distribution can similarly be assessed by in vitro or in situ hybridization to VHR transcripts. These are conventional techniques well within the grasp of those skilled in the art. Ausubel et al., Chapters 2, 4 and 14 (1992)

The DNA probes that would be useful in the above-noted hybridization studies may be derived from any portion of the 555 nucleotides of the VHR coding sequence and are generally at least about fifteen nucleotides in length. Therefore, probes are specifically contemplated that comprise nucleotides 29 to 43, or 30 to 44, or 31 to 45 and so forth up to a probe comprising 569 to 583 of the nucleotide sequence of FIG. 2B (SEQ ID NO. 1). Thus, each probe would comprise at least about 15 linear nucleotides of the nucleotide sequence of FIG. 2B (SEQ ID NO:2), designated by the formula "n+28 to n+42," where n is an integer from 1 to 541. Longer probes that hybridize to the VHR gene under high stringency conditions (6X SSC, 68° C.) are also contemplated, including those that comprise the entire nucleotide sequence of FIG. 2B (SEQ ID NO:2).

Assays for the VHR protein itself can also determine tissue distribution and expression level for diagnostic purposes. This is accomplished by producing polyclonal or monoclonal antibodies to VHR and assessing binding of the antibodies to tissues, cells or cell extracts. These are also conventional techniques well within the grasp of those skilled in the art. Ausubel et al., Chapter 14 (1992). Comparing the results of any of these studies on diseased tissue with those obtained using normal tissue would provide evidence of VHR-involvement with disease.

Similarly, VHR and the corresponding nucleic acids can be used in the treatment of a VHR-related disease. This can be accomplished with nucleic acids, for example, by gene transfer techniques. Sense or antisense RNA's for normal VHR are expressed in cells that lack VHRRNA or produce an excess of the VHR RNA, respectively, thereby permitting expression of VHR protein at non-pathologic levels and reducing or eliminating symptoms of the VHR-related disease.

Administration of the VHR protein to a subject with a VHR-related disease, via any common route (oral, nasal, buccal, rectal, vaginal, or topical), or by subcutaneous, intramuscular, intraperitoneal, or intravenous injection, can improve a disease state where VHR function is lacking. These proteins could be produced in cultures of transformed prokaryotic or eukaryotic cells. The DNA's used to transform cells would preferably comprise a nucleotide sequence corresponding to the amino acid sequence, that is optimized for the host of choice in terms of codon usage, initiation of transcription and translation, and expression of commercially useful amounts of VHR. Ausubel et al., Chapter 16 (1992). Degeneracy in codons for most amino acids means that other nucleotide sequences besides that disclosed in FIG. 2B can encode VHR. Such nucleotide sequences would have the same utility in the production of VHR as the sequence disclosed in FIG. 2B (SEQ ID NO:2).

Finally, polyclonal or monoclonal antibodies which bind to the VHR protein can be administered to a subject suffering from a VHR-related disease. If excess amounts of the VHR were present in the subject's bloodstream, for example, antibody treatment could facilitate removal of VHR therefrom.

VHR polypeptides and antibodies would-be delivered in effective amounts, i.e., in amounts that reduce the symptoms of the VHR-related disease. VHR polypeptides and antibodies reactive therewith would normally be administered in a pharmaceutically acceptable carrier, such carriers being well known in the art. One common carrier is saline solution.

EXAMPLES

Other objects, features and advantages of the present invention will become apparent from the following Examples. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Example 1

Plasmid construction of a bek kinase. The EcoRI-SalI fragment of the mouse KGF receptor cDNA, described by Miki et al., *Science* 251:72–75 (1991), which includes the kinase and carboxy-terminal domains (residues 361-707), was ligated to the EcoRI-SalI fragment of the expression vector pCEV-lacZ to generate the plasmid pCEV-bek (FIG. 1). pCEV-lacZ is a pUC-based plasmid expression vector which produces a β-gal fusion protein under the control of the lac promoter (see below). The resulting β-gal-bek fusion product is autophosphorylating.

Construction of λpCEV-laCZ. Drokaryotic expression vector. The vector designed for prokaryotic cDNA expression cloning was similar to λgt11, but incorporated several additional features. cDNA's can be inserted by the automatic directional cloning method, allowing construction of unidirectional libraries with high efficiency. Miki et al. (1989). Use of unidirectional libraries to screen negative signals excludes anti-sense cDNA clones which might inhibit the expression of cDNA's in host cells, like the bek kinase used in these experiments.

To construct λpCEV-lacZ, the lacZ structural gene of pMC1871 (Pharmacia) was cloned into pUC-SVneo4ΔRI, a precursor plasmid of pCEV27. Miki et al., *Proc. Nat'l Acad. Sci. U.S.A.* 88:5167–5171 (1991). Multiple cloning sites similar to those in λpCEV27 were created by inserting oligonucleotides in the EcoRI site of the lacZ gene. The resulting plasmid, pCEV-lacZ, was linearized at the NotI site, multiple excision sites were attached as described by Miki et al. (PNAS 1991), and it was then cloned into λpCEV27 NotI arms to create λpCEV-lacZ.

Library construction and screening. An oligo(dT) primed M246 human fibroblast cDNA library was constructed in λpCEV-lacZ. Ishibashi et al., *Proc. Nat'l Acad. Sci. U.S.A.* in press (1992). To screen a library, bacteria (Y1091, Clontech) containing the pCEV-bek plasmid were infected with phage (1.2×10⁴ plaques per 150 mm plate) and grown on plates containing ampicillin (50 μg/ml) at 37° C. for four hours. The plates were overlaid with nitrocellulose filters impregnated with 10 mM isopropyl-β-D thiogalactopyranoside (IPTG), and incubated for an additional four hours at 37° C., as described previously. Macgregor et al., *Oncogene* 5:451–458 (1990). The filters were removed, washed with phosphate buffered saline (PBS) containing 0.05% Tween-20 (PBST), and then blocked in PBST containing 3% dry milk for one hour at room temperature. Filters were probed with mouse monoclonal anti-pTyr (Upstate Biotechnology, Inc.) overnight at room temperature, rinsed four times with PBST, detected with [$^{125}$I]-protein A for 30 minutes, rinsed again, dried, and exposed to Kodak XAR film at –80° C. overnight. A total of 4.5×10⁵ plaques were screened. Several clones displayed decreased signal intensity, and in two clones, designated 12 and 27, anti-pTyr recognition was completely abolished. Dot blot hybridization under high stringency conditions suggested that these two clones contained overlapping cDNA inserts. Clone 27, which contained the larger cDNA insert (4.1 kB) was analyzed further.

Example 2

Phosphatase assays with bacterial extracts. Plasmids carrying cDNA inserts were rescued from the isolated phagemid clones 12 and 27 as described previously. Miki et al. (1989). Cultures of *E. coli* strain Y1091 (50 ml), carrying either pCEV-bek, pCEV-lacZ (pCEV-lacZ vector without an insert), or pCEV27 were grown and induced with 1 mM IPTG as described. Guan and Dixon, *Anal. Biochem.* 192:262–267 (1991). Cells were collected by centrifugation and lysed in 1 ml of buffer containing 50 mM HEPES, pH 7.4, 1% Triton X-100, and 1 mM phenylmethylsulfonyl fluoride. Lysates were sonicated twice for ten seconds each, clarified by centrifugation, and the supernatants were tested for phosphatase activity.

Phosphatase activity was determined by incubation of about 40 μl of *E. coli* extract from pCEV-bek with 10 μl of *E. coli* extract from pCEV-lacZ or pCEV test clone with or without 3 mM sodium vanadate at 37° C. for 30 minutes. The reaction was stopped by boiling in sodium dodecyl sulfate polyacrylamide gel electrophoresis (SDS-PAGE) sample buffer, described by Laemmli, *Nature* 227:680–685 (1970), for three minutes. The Sample was divided into two equal aliquots, resolved by 6.5% SDS-PAGE, and transferred to Immobilon (Milipore).

Immunoblotting was performed with monoclonal anti-pTyr (Upstate Biotechnology, Inc.) or monoclonal anti-β-gal antibodies (Promega) as described previously. Bottaro et al., *J. Biol. Chem.* 263:12767–12770 (1990). The results showed that the pTyr content of β-gal-bek was dramatically reduced by clone 27 lysate and that this effect was inhibited by sodium vanadate, a known inhibitor of tyrosine phosphatases. In addition, it should be noted that clone 27 lysates did not reduce the level of β-gal-bek, arguing against the possibility that pCEV27 encodes a protease. Together, these data imply that pCEV27 encodes a functional PTP.

DNA sequencing and sequence analysis. Plasmids carrying cDNA inserts were sequenced in both directions using T7 polymerase (U.S. Biochemical) by the dideoxy-termination method. Sanger et al., *Proc. Nat'l Acad. Sci. U.S.A.* 74:5463–5467 (1977). Comparison of sequences to the data bases was performed using the blast program. AltsChul et al., *J. Mol. Biol.* 215:403–410 (1990).

pCEV12 and pCEV27 had inserts of 1.8 kB and 4.1 kB, respectively. Sequence analysis confirmed that they were overlapping cDNA's of the same gene (FIG. 2). Northern analysis of M246 total RNA revealed a single transcript of about 4.1 kB recognized by the clone 27 CDNA probe, suggesting that clone 27 encompassed the entire VHR gene (data not show). Nucleotide sequencing of the 4.1 kB insert revealed a short GC-rich 5'-untranslated region, an open reading frame predicting translation product of a 185 residues, and a long 3'-untranslated sequence containing a polyadenylation signal (FIG. 2 (SEQ ID NO:1). The ATG codon at nucleotides 29-31 is the most likely start site for translation, according to Kozak criteria for authentic initiation codons. Kozak, *Nucl. Acid ReS.* 15:8125-8148 (1987). A stop codon is present at nucleotide 584-586.

The amino acid sequence predicted from the VHR cDNA lacked an N-terminal signal peptide Consensus sequence or a characteristic transmembrane sequence. Accordingly, VHR is likely to be a cytosolic, soluble PTP. Comparison of VHR with protein sequences in several databases revealed similarity to the recently published 3CH134 gene, Charles et al., *Oncogene* 7:187-190 (1992), and vaccinia virus phosphatase VH1. Guan et al. (*Nature* 1991). The former is a serum-induced early response gene with no known function, and the latter is a novel viral enzyme which dephosphorylates both serine and tyrosine residues in vitro. A 30 amino acid stretch of VHR (codons 115-144 of Seq ID NO:2)) exhibited 50% identity to VH1 (FIG. 3 (SEQ ID NOS 3 and 5). This domain includes a motif, HCXXXXXR (residues 66-73 of SEQ ID NO:3, residues 64-71 of SEQ ID NO:4, and residues 64-71 of SEQ ID NO:5), where X is any amino acid, which is found in all known PTP's and is thought to include the catalytic site. The cysteine and arginine residues in this motif are essential to phosphatase activity. Streuli et al., *EMBO J.* 9:23399-2407 (1990); Strausfeld et al., *Nature* 351:242-245 (1991). Outside of this region, there was little if any sequence similarity with VH1. Beyond a 15 amino acid stretch encompassing the motif, there was no detectable similarity with any other known phosphatase.

Example 3

Production and purification of bacterially-expressed VHR. A 0.8 kB SalI-HinDIII fragment containing the entire VHR coding region was blunt-ended with DNA polymerase (Klenow fragment), and BamHI linkers were added. DNA was digested with BamHI, and inserted in-frame into the BamHI site of the pGEX-KT expression vector, described in Hakes et al., *Anal. Biochem.* 202:293-298 (1992), to produce pGEX-VHR. Plasmid pGEX-VHR was used to express VHR as a fusion protein with glutathione-S-transferase (GST). Expression and purification of GST-VHR was performed as described for a rat brain PTP. Guan et al. (*Anal. Biochem.* 1991). GST-VHR was >98% pure as determined by Coomassie Blue staining of SDS-PAGE gels. VHR protein, obtained by thrombin cleavage of the purified GST fusion protein, was used for phosphatase assays.

Phosphatase assays with purified VHR. Dephosphorylation of p-nitrophenylphosphate (pNPP) was performed as described previously. Tonks et al., *J. Biol. Chem.* 263:6731-6737 (1988).

Receptor-tyrosine kinases from epidermal growth factor (EGF), platelet-derived growth factor (PDGF), keratinocyte growth factor (KGF), and insulin expressed in NIH/3T3 fibroblasts were stimulated with their respective ligands in situ-and partially purified as follows. Cells (2 mg protein) were lysed with 1% Triton X-100 containing protease and phosphatase inhibitors at 0° C., and the lysates were clarified by centrifugation. Phosphotyrosine-containing proteins were immunoprecipitated with monoclonal anti-pTyr agarose (Upstate Biotechnology, Inc.) for two hours at 4° C., and the beads were washed three times in lysing buffer, and then twice in the same buffer without phosphatase inhibitors. Proteins were eluted with 50 µl of 100 mM glycine, pH 2.5, neutralized with 2 µl 1.5 M Tris, pH 9.0, and treated with purified GST-VHR or GST alone (1 µg) for ten minutes at 25° C. Samples were then boiled in sample buffer, separated by SDS-PAGE, transferred to PVDF membrane, immunob-lotted with anti-pTyr and detected with [$^{125}$I]-protein A. Autoradiographic imaging and quantitation was performed using a Molecular Dynamics PhosphorImager. Blots processed in parallel and probed with appropriate anti-receptor antibodies were used to identify receptor protein bands, and to confirm that the amount of receptor protein was unchanged following phosphatase treatment.

Baculovirus-expressed PDGF was purified to homogeneity as described previously. Receptor (1-100 nM) was treated with VHR in 50 mM imidazole, pH 7.5 containing 0.1% 2-mercaptoethanol for ten minutes at 25° C. Reactions were stopped by addition of boiling SDS-PAGE sample buffer and samples were subjected to SDS-PAGE and anti-pTyr/[$^{125}$I] -protein A immunoblotting. Dephosphorylation was quantitated using a Molecular Dynamics PhosphorImager.

Whereas GST alone was devoid of phosphatase activity, the GST-VHR fusion protein hydrolyzed this substrate rapidly with a $K_m$ in the micromolar range (FIG. 4). The $K_m$ was unchanged after cleavage of the VHR from GST with thrombin (data not shown). pNPP hydrolysis by the phosphatase was completely inhibited in the presence of 1 mM sodium vanadate. Okadaic acid and sodium fluoride, at similar concentrations, had no inhibitory effect on the enzyme activity. All these properties are characteristic of tyrosine phosphatases. Fischer et al. (1991); Hunter et al. (1989).

The interaction of this VHR with several tyrosine-phosphorylated growth factor receptors was determined. Autophosphorylated receptors for PDGF, EGF, insulin and KGF were immunoprecipitated with anti-pTyr-agarose, eluted with low pH buffer, neutralized, and treated with purified VHR or GST. Following incubation, samples were subjected to SDS-PAGE and immunoblotted with anti-pTyr. A dramatic decrease in the anti-pTyr staining of all four receptors, as well as other pTyr-containing proteins in the same samples following incubation with VHR was seen. Immunoblotting of parallel samples with the appropriate receptor antibodies showed that the amount of receptor in GST- and VHR-treated samples was identical (data not shown). Further analysis of VHR phosphatase activity on highly purified PDGF receptor indicated that the $K_m$ of this interaction was below 100 mM.

Example 4

Serine phosphatase activity. Casein was phosphorylated with [$^{32}$P]-ATP by cAMP-dependent protein kinase and enzymatically dephosphorylated as described previously. serine-specific phosphorylation of casein was -confirmed by phosphoamino acid analysis. Boyle et al., *Methods Enzymol.* 201:110-149 (1991).

Figure 5:
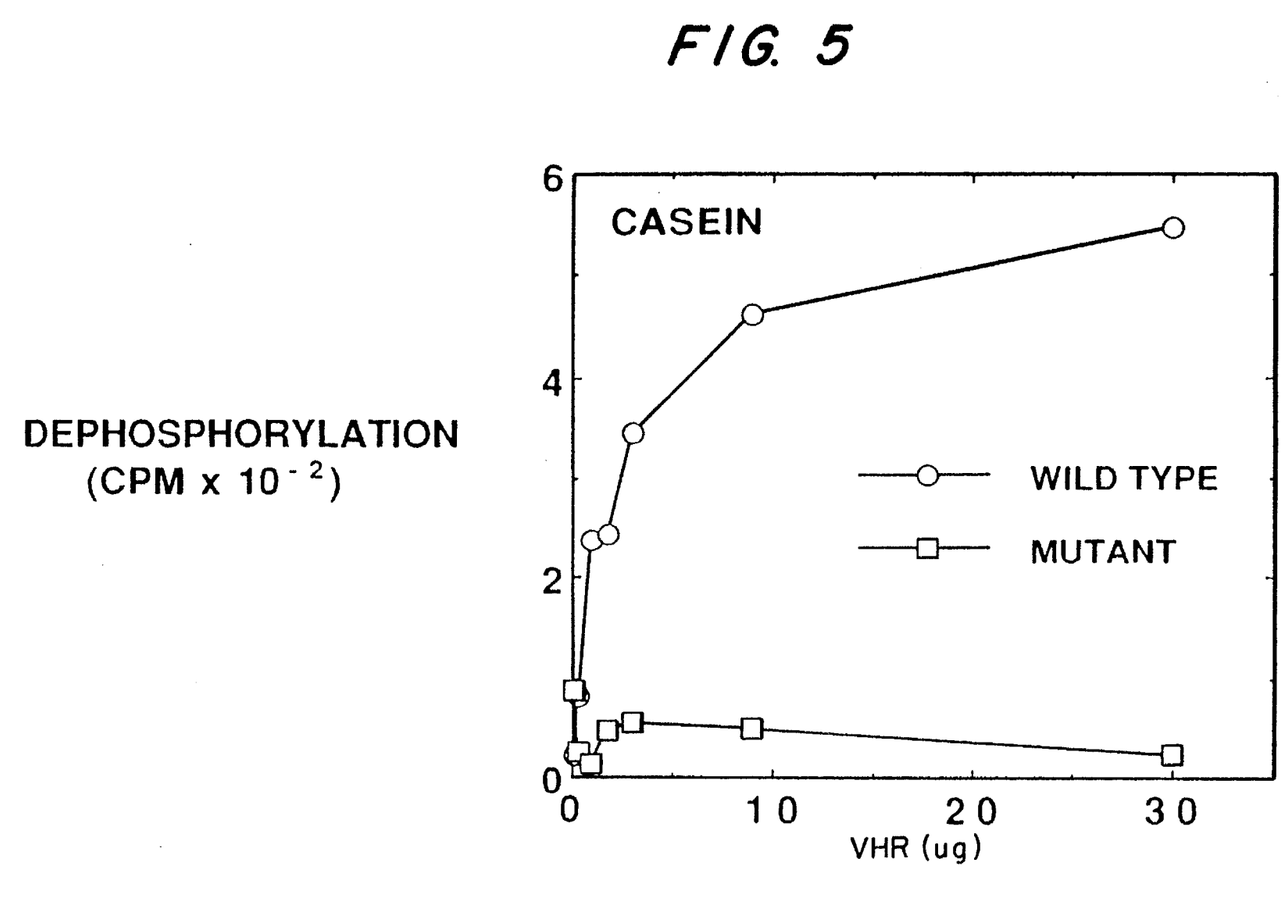

Although VHR showed only limited similarity to VH1, the possibility that VHR also possessed serine phosphatase activity was examined. In fact, VHR effectively dephosphorylated serine-phosphorylated casein (FIG. 5). All of these findings indicated that VHR had dual specificity for phosphotyrosine and phosphoserine residues.

Site-directed mutagenesis. In order to examiner the importance of the cysteine residue in VHR (residue 124), the oligonucleotide 5'-TGCTCGTCCACTCCCGGGAAG-GTTA-3'(SEQ ID NO:7) was use to mutate VHR codon Cys 124 to Ser. A 0.8 KB SalI-HinDIII fragment containing the entire coding region of VHR was subcloned into our M13 vector. Site-directed mutagenesis was performed using the *In Vitro* Mutagenesis Kit (U.S. Biochemical) according to the manufacturer's protocol. The mutation was confirmed by DNA sequencing. A fragment containing the mutation was subsequently cloned into pGEX-KT to produce mutant VHR protein.

VHR-Ser 124 was purified and examined for its ability to dephosphorylate pNPP and casein exactly as for wild-type VHR. The substitution resulted in complete loss of activity toward pNPP (data not shown) and casein (FIG. 5).

---

We claim:

1. A method for identifying a DNA encoding a protein phosphatase, comprising
   (a) providing an autophosphorylating protein tyrosine kinase,
   (b) transfecting or infecting a bacterial host with a phagemid comprising
      (i) an origin of replication;
      (ii) a DNA test molecule; and
      (iii) a regulatory region which results in the expression of a test protein encoded by said DNA test molecule,
   (c) culturing the transfected or infected bacterial host in the presence of the phosphorylated form of said autophosphorylating protein tyrosine kinase such that phagemid-induced plaques are formed and said autophosphorylating protein tyrosine kinase and said test protein are brought in contact with each other;
   (d) screening the resulting phagemid plaques to identify plaques that contain the unphosphorylated form of said autophosphorylating protein tyrosine kinase; and
   (e) isolating phagemid DNA from plaques which contain the unphosphorylated form of said autophosphorylating protein tyrosine kinase, whereby said isolated-phagemid DNA encodes said protein phosphatase.

2. A method according to claim 1, wherein said screening comprises treating said plaques with antibodies that bind the phosphorylated form of said autophosphorylating protein tyrosine kinase and do not bind the unphosphorylated form of said autophosphorylating protein tyrosine kinase.

3. A method according to claim 2, wherein said antibodies are polyclonal antibodies.

4. A method according to claim 2, wherein said antibodies are monoclonal antibodies.

5. A method according to claim 1, wherein said autophosphorylating protein tyrosine kinase is the β-gal-bek fusion protein.

6. A method for identifying a DNA encoding a protein phosphatase, comprising
   (a) providing an autophosphorylating protein tyrosine kinase,
   (b) transforming a bacterial host with a plasmid comprising
      (i) an origin of replication;
      (ii) a selectable marker;
      (iii) a DNA test molecule; and
      (iv) a regulatory region which results in the expression of a test protein encoded by said DNA test molecule,
   (c) culturing the transformed bacterial host, in the presence of the phosphorylated form of said autophosphorylating protein tyrosine kinase, under selective conditions, such that plasmid-containing colonies are formed;
   (d) treating said colonies to bring said autophosphorylating protein tyrosine kinase and said test protein in contact with each other;
   (e) screening said colonies to identify colonies that contain the unphosphorylated form of said autophosphorylating protein tyrosine kinase; and
   (f) isolating plasmid DNA from colonies which contain the unphosphorylated form of said autophosphorylating protein tyrosine kinase, whereby said isolated-plasmid DNA encodes said protein phosphatase.

7. A method according to claim 6, wherein said screening comprises treating said colonies with antibodies that bind the phosphorylated form of said autophosphorylating protein tyrosine kinase and do not bind the unphosphorylated form of said autophosphorylating protein tyrosine kinase.

8. A method according to claim 7, wherein said antibodies are polyclonal antibodies.

9. A method according to claim 7, wherein said antibodies are monoclonal antibodies.

10. A method according to claim 6, wherein said autophosphorylating protein tyrosine kinase is the β-gal-bek fusion protein.

11. A method according to claim 6, wherein said selection is antibiotic treatment.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 861 base pairs
        ( B ) TYPE: nucleic acid
        ( C ) STRANDEDNESS: double
        ( D ) TOPOLOGY: linear     ( i x ) FEATURE:
        ( A ) NAME/KEY: CDS
        ( B ) LOCATION: 29..586

( x i ) SEQUENCE DESCRIPTION: SEQ ID NO:1:

```
GCCGGGCGTG CAGGGCCCCG CCGCCGCC ATG TCG GGC TCG TTC GAG CTC TCG                52
                                Met Ser Gly Ser Phe Glu Leu Ser
                                 1               5

GTG CAG GAT CTC AAC GAC CTG CTC TCG GAC GGC AGC GGC TGC TAC AGC               100
Val Gln Asp Leu Asn Asp Leu Leu Ser Asp Gly Ser Gly Cys Tyr Ser
         10              15              20

CTC CCG AGC CAG CCC TGC AAC GAG GTC ACC CCG CGG ATC TAC GTG GGC               148
Leu Pro Ser Gln Pro Cys Asn Glu Val Thr Pro Arg Ile Tyr Val Gly
 25              30              35                              40

AAC GCG TCT GTG GCT CAG GAC ATC CCC AAG CTG CAG AAA CTA GGC ATC               196
Asn Ala Ser Val Ala Gln Asp Ile Pro Lys Leu Gln Lys Leu Gly Ile
                 45              50                      55

ACC CAT GTG CTG AAC GCG GCT GAG GGC AGG TCC TTC ATG CAC GTC AAC               244
Thr His Val Leu Asn Ala Ala Glu Gly Arg Ser Phe Met His Val Asn
                 60              65              70

ACC AAT GCC AAC TTC TAC AAG GAC TCC GGC ATC ACA TAC CTG GGC ATC               292
Thr Asn Ala Asn Phe Tyr Lys Asp Ser Gly Ile Thr Tyr Leu Gly Ile
         75              80              85

AAG GCC AAC GAC ACA CAG GAG TTC AAC CTC AGC GCT TAC TTT GAA AGG               340
Lys Ala Asn Asp Thr Gln Glu Phe Asn Leu Ser Ala Tyr Phe Glu Arg
         90              95              100

GCT GCC GAC TTC ATT GAC CAG GCT TTG GCT CAA AAG AAT GGC CGG GTG               388
Ala Ala Asp Phe Ile Asp Gln Ala Leu Ala Gln Lys Asn Gly Arg Val
105              110             115                             120

CTC GTC CAC TGC CGG GAA GGT TAT AGC CGC TCC CCA ACG CTA GTT ATC               436
Leu Val His Cys Arg Glu Gly Tyr Ser Arg Ser Pro Thr Leu Val Ile
                 125             130                     135

GCC TAC CTC ATG ATG CGG CAG AAG ATG GAC GTC AAG TCT GCC CTG AGC               484
Ala Tyr Leu Met Met Arg Gln Lys Met Asp Val Lys Ser Ala Leu Ser
                 140             145                     150

ATC GTG AGG CAG AAC CGT GAG ATC GGC CCC AAC GAT GGC TTC CTG GCC               532
Ile Val Arg Gln Asn Arg Glu Ile Gly Pro Asn Asp Gly Phe Leu Ala
                 155             160                     165

CAG CTC TGC CAG CTC AAT GAC AGA CTA GCC AAG GAG GGG AAG TTG AAA               580
Gln Leu Cys Gln Leu Asn Asp Arg Leu Ala Lys Glu Gly Lys Leu Lys
                 170             175                     180

CCC TAGGGCACCC CCACCGCCTC TGCTCGAGAG GTCCGTGGGG GAGGCCGTGG                     633
Pro
```

185

| GAAAGGTGTC | CGAGCTGCCA | TGTTTAGGAA | ACACACTGTA | CCCTGCTCCC | AGCATCACAA | 693 |
| GGCACTTGTC | TACAAGTGTG | TCCCAACACA | GTCCTGGGCC | ACTTTCCCCA | CCCTGGGGAG | 753 |
| CACATAAAGA | AGCTTGCCAA | GGGGGGCGTC | CTTGCTCCCC | AGTTGTCCTG | TTTCTGTAAC | 813 |
| TTATGATGTC | TTTTCCCTGA | GATGGGGGCT | CAGAGGGGGA | AGGCCTGT | | 861 |

(2) INFORMATION FOR SEQ ID NO:2:

(i) SEQUENCE CHARACTERISTICS:
        (A) LENGTH: 185 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Ser Gly Ser Phe Glu Leu Ser Val Gln Asp Leu Asn Asp Leu Leu
 1               5                  10                  15

Ser Asp Gly Ser Gly Cys Tyr Ser Leu Pro Ser Gln Pro Cys Asn Glu
             20                  25                  30

Val Thr Pro Arg Ile Tyr Val Gly Asn Ala Ser Val Ala Gln Asp Ile
         35                  40                  45

Pro Lys Leu Gln Lys Leu Gly Ile Thr His Val Leu Asn Ala Ala Glu
     50                  55                  60

Gly Arg Ser Phe Met His Val Asn Thr Asn Ala Asn Phe Tyr Lys Asp
 65                  70                  75                  80

Ser Gly Ile Thr Tyr Leu Gly Ile Lys Ala Asn Asp Thr Gln Glu Phe
                 85                  90                  95

Asn Leu Ser Ala Tyr Phe Glu Arg Ala Ala Asp Phe Ile Asp Gln Ala
                100                 105                 110

Leu Ala Gln Lys Asn Gly Arg Val Leu Val His Cys Arg Glu Gly Tyr
             115                 120                 125

Ser Arg Ser Pro Thr Leu Val Ile Ala Tyr Leu Met Met Arg Gln Lys
     130                 135                 140

Met Asp Val Lys Ser Ala Leu Ser Ile Val Arg Gln Asn Arg Glu Ile
145                 150                 155                 160

Gly Pro Asn Asp Gly Phe Leu Ala Gln Leu Cys Gln Leu Asn Asp Arg
                165                 170                 175

Leu Ala Lys Glu Gly Lys Leu Lys Pro
             180                 185
```

(2) INFORMATION FOR SEQ ID NO:3:

(i) SEQUENCE CHARACTERISTICS:
        (A) LENGTH: 118 amino acids
        (B) TYPE: amino acid
        (D) TOPOLOGY: linear     (xi) SEQUENCE DESCRIPTION: SEQ ID NO:3:

```
Val Leu Asn Ala Ala Glu Gly Arg Ser Phe Met His Val Asn Thr Asn
 1               5                  10                  15

Ala Asn Phe Tyr Lys Asp Ser Gly Ile Thr Tyr Leu Gly Ile Lys Ala
             20                  25                  30

Asn Asp Thr Gln Glu Phe Asn Leu Ser Ala Tyr Phe Glu Arg Ala Ala
         35                  40                  45

Asp Ile Phe Ile Asp Gln Ala Leu Ala Gln Lys Asn Gly Arg Val Leu
     50                  55                  60
```

```
Val His Cys Arg Glu Gly Tyr Ser Arg Ser Pro Thr Leu Val Ile Ala
65                  70              75                      80

Tyr Leu Met Met Arg Gln Lys Met Asp Val Lys Ser Ala Leu Ser Ile
            85              90                      95

Val Arg Gln Asn Arg Glu Ile Gly Pro Asn Asp Gly Phe Leu Ala Gln
        100             105                     110

Leu Cys Gln Leu Asn Asp
        115
```

(2) INFORMATION FOR SEQ ID NO:4:

(i) SEQUENCE CHARACTERISTICS:
        (A) LENGTH: 117 amino acids
        (B) TYPE: amino acid
        (D) TOPOLOGY: linear     (xi) SEQUENCE DESCRIPTION: SEQ ID NO:4:

```
Met Leu Asp Ala Leu Gly Ile Thr Ala Leu Ile Asn Val Ser Ala Asn
1               5                   10                  15

Cys Pro Asn His Phe Glu Gly His Tyr Gln Tyr Lys Ser Ile Pro Val
            20              25                  30

Glu Asp Asn His Lys Ala Asp Ile Ser Ser Trp Phe Asn Glu Ala Ile
            35              40                  45

Asp Phe Ile Asp Ser Ile Lys Asp Ala Gly Gly Arg Val Phe Val His
        50              55                  60

Cys Gln Ala Gly Ile Ser Arg Ser Ala Thr Ile Cys Leu Ala Tyr Leu
65                  70              75                      80

Met Arg Thr Asn Arg Val Lys Leu Asp Glu Ala Phe Glu Phe Val Lys
            85              90                      95

Gln Arg Arg Ser Ile Ile Ser Pro Asn Phe Ser Phe Met Gly Gln Leu
        100             105                     110

Leu Gln Phe Glu Ser
        115
```

(2) INFORMATION FOR SEQ ID NO:5:

(i) SEQUENCE CHARACTERISTICS:
        (A) LENGTH: 116 amino acids
        (B) TYPE: amino acid
        (D) TOPOLOGY: linear     (xi) SEQUENCE DESCRIPTION: SEQ ID NO:5:

```
Pro Ser Ser Glu Val Lys Phe Lys Tyr Val Leu Asn Leu Thr Met Asp
1               5                   10                  15

Lys Tyr Thr Leu Pro Asn Ser Asn Ile Asn Ile His Ile Pro Leu
            20              25                  30

Val Asp Asp Thr Thr Thr Asp Ile Ser Lys Tyr Phe Asp Asp Val Thr
            35              40                  45

Ala Phe Leu Ser Lys Cys Asp Gln Arg Asn Glu Pro Val Leu Val His
        50              55                  60

Cys Ala Ala Gly Val Asn Arg Ser Gly Ala Met Ile Leu Ala Tyr Leu
65                  70              75                      80

Met Ser Lys Asn Lys Glu Ser Leu Pro Met Leu Tyr Phe Leu Tyr Val
            85              90                      95

Tyr His Ser Met Arg Asp Leu Arg Gly Ala Phe Val Glu Asn Pro Ser
            100             105                     110

Phe Lys Arg Gln
        115
```

( 2 ) INFORMATION FOR SEQ ID NO:6:

( i ) SEQUENCE CHARACTERISTICS:
      ( A ) LENGTH: 45 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:6:

GTGCTCGTCC ACTGCCGGGA AGGTTATAGC CGCTCCCCAA CGCTA     45

( 2 ) INFORMATION FOR SEQ ID NO:7:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:7:

TGCTCGTCCA CTCCCGGGAA GGTTA     25